United States Patent
Pandolfino et al.

(10) Patent No.: US 10,898,091 B2
(45) Date of Patent: Jan. 26, 2021

(54) SYSTEMS, METHODS, AND APPARATUS FOR ESOPHAGEAL PANOMETRY

(71) Applicant: Northwestern University, Evanston, IL (US)

(72) Inventors: John Erik Pandolfino, Chicago, IL (US); Zhiyue Lin, Chicago, IL (US); Peter J. Kahrilas, Chicago, IL (US); John O'Dea, Galway (IE); Adrian McHugh, Galway (IE)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 15/546,986

(22) PCT Filed: Feb. 2, 2016

(86) PCT No.: PCT/US2016/016161
§ 371 (c)(1),
(2) Date: Jul. 27, 2017

(87) PCT Pub. No.: WO2016/126701
PCT Pub. Date: Aug. 11, 2016

(65) Prior Publication Data
US 2018/0008156 A1 Jan. 11, 2018

Related U.S. Application Data

(60) Provisional application No. 62/110,867, filed on Feb. 2, 2015.

(51) Int. Cl.
*A61B 5/03* (2006.01)
*A61B 5/053* (2006.01)
(Continued)

(52) U.S. Cl.
CPC .............. *A61B 5/037* (2013.01); *A61B 1/273* (2013.01); *A61B 5/0538* (2013.01);
(Continued)

(58) Field of Classification Search
CPC ........ A61B 5/053; A61B 5/037; A61B 5/4233
See application file for complete search history.

(56) References Cited

U.S. PATENT DOCUMENTS 9,474,482 B2 * 10/2016 Devanaboyina ..... A61B 5/0024
2001/0053920 A1 12/2001 Shaker
(Continued)

FOREIGN PATENT DOCUMENTS

WO 2008027913 3/2008
WO 2016126701 8/2016

OTHER PUBLICATIONS

Gregersen et al. "Balloon-Distension Studies in the Gastrointestinal Tract: Current Role." Dig Dis. 2006;24(3-4):286-96. (Year: 2006).*
(Continued)

*Primary Examiner* — Meredith Weare
(74) *Attorney, Agent, or Firm* — Pearl Cohen Zedek Latzer Baratz LLP

(57) ABSTRACT

Systems, methods, and apparatus for esophageal panometry are provided. An example method includes capturing measurement data including an area and a pressure of an esophageal body via a measurement device positioned with respect to the esophageal body; generating representations of the exported measurement data; analyzing the measurement data to determine esophageal reactivity based on the area and pressure; assessing esophageal function based on the determined esophageal reactivity; and outputting an indication of esophageal function.

13 Claims, 10 Drawing Sheets

(51) Int. Cl.
*A61B 5/00* (2006.01)
*A61B 1/273* (2006.01)
(52) U.S. Cl.
CPC .......... *A61B 5/4233* (2013.01); *A61B 5/6853* (2013.01); *A61B 5/687* (2013.01)

(56) References Cited

U.S. PATENT DOCUMENTS

| | | | |
|---|---|---|---|
| 2008/0027358 A1* | 1/2008 | Gregersen | A61B 5/036 600/593 |
| 2008/0275368 A1* | 11/2008 | Gregersen | A61B 5/1107 600/593 |
| 2010/0113939 A1 | 5/2010 | Mashimo et al. | |
| 2011/0082488 A1 | 4/2011 | Niazi | |
| 2012/0016256 A1 | 1/2012 | Mabary et al. | |
| 2013/0046150 A1* | 2/2013 | Devanaboyina | A61B 5/0476 600/301 |

OTHER PUBLICATIONS

Liao et al. "Distension-Evoked Motility Analysis in Human Esophagus." Neurogastroenterol Motil. May 2013;25(5):407-12, e296-7. Epub Jan. 29, 2013. (Year: 2013).*

"FAQs about Swallowing Disoders." Johns Hopkins Medicine. Jun. 12, 2013. 2 pages. https://web.archive.org/web/20130612055844/https://www.hopkinsmedicine.org/gastroenterology_hepatology/diseases_conditions/faqs/swallowing_disorders.html. (Year: 2013).*

Hirano et al. "Functional Lumen Imaging Probe for the Management of Esophageal Disorders: Expert Review From the Clinical Practice Updates Committee of the AGA Institute." Clin Gastroenterol Hepatol. Mar. 2017;15(3):325-334. (Year: 2017).*

Ata-Lawenko. "Emerging Roles of the Endolumenal Functional Lumen Imaging Probe in Gastrointestinal Motility Disorders." J Neurogastroenterol Motil. Apr. 30, 2017;23(2):164-170. (Year: 2017).*

Lin et al. "Functional Luminal Imaging Probe Topography: An Improved Method for Characterizing Esophageal Distensibility in Eosinophilic Esophagitis." Therap Adv Gastroenterol. Mar. 2013;6(2):97-107. (Year: 2013).*

Chen et al. "Relevance of Ineffective Esophageal Motility to Secondary Peristalsis in Patients with Gastroesophageal Reflux Disease." J Gastroenterol Hepatol. Feb. 2014;29(2):296-300. (Year: 2014).*

International Searching Authority, "Search Report", issued in connection with PCT Patent application No. PCT/ US2016/016161, dated May 9, 2016, 6 pages.

International Searching Authority, "Written Opinion", issued in connection with PCT Patent application No. PCT/ US2016/016161, dated May 9, 2016, 6 pages.

Regan, "New measures of upper esophageal sphincter distensibility and opening patterns during swallowing in healthy subjects using EndoFLIP", Jan. 31, 2012, Blackwell Publishing, 10 pages.

Rogers et al., "The Effect of Volumetric Distention on Esophageal Function in Eosinophillic Esophagitis As Compared with Healthy Controls", Digestive Disease Week 2014, 1 page.

Gregersen et al., "New High-Resolution Functional Luminal Imaging System for the Oesophago-Gastric Junction", Aalborg Hospital, last retrieved on Jul. 27, 2017, 1 page.

International Bureau, "International Preliminary Report on Patentability", issued in connection with PCT patent application No. PCT/US2016/016161, dated Aug. 17, 2017, 8 pages.

* cited by examiner

SYSTEMS, METHODS, AND APPARATUS FOR ESOPHAGEAL PANOMETRY

CROSS-REFERENCE TO RELATED APPLICATIONS

This application claims the benefit of priority to PCT Patent Application No. PCT/US16/16161, entitled "SYSTEMS, METHODS, AND APPARATUS FOR ESOPHAGEAL PANOMETRY", filed on Feb. 2, 2016, which claims the benefit of priority to U.S. Patent Application Ser. No. 62/110,867, entitled "SYSTEMS, METHODS, AND APPARATUS FOR ESOPHAGEAL PANOMETRY", filed on Feb. 2, 2015, each of which is incorporated herein by reference in its entirety for all purposes.

STATEMENT REGARDING FEDERALLY SPONSORED RESEARCH OR DEVELOPMENT

This invention was made with government support under DK079902 awarded by the National Institutes of Health. The government has certain rights in the invention.

FIELD

The presently described technology generally relates to evaluation of esophageal function. In particular, the presently described technology relates to systems, methods, and apparatus for esophageal panometry to process and display data to provide an evaluation of esophageal function.

BACKGROUND

A human esophagus moves food from a person's mouth to his or her stomach. The esophagus includes muscles that move the food by contracting in a particular rhythm to form a sweeping wave that moves the food down the length of the tubular esophagus into the stomach. The sweeping wave of contraction is typically referred to as peristalsis.

The esophagus is divided into a plurality of segments. An upper esophageal sphincter (UES) is located at an upper end of the esophagus. The UES is a muscle that functions as a valve to regulate food entering the esophagus from the pharynx. A lower esophageal sphincter (LES) is located at a lower end of the esophagus. The LES is a muscle that functions as a valve to regulate food leaving the esophagus to enter the stomach. The LES protects the lower esophagus from stomach acid and bile, for example, which can cause discomfort or damage the esophagus.

The end of the esophagus is surrounded by a thin muscle referred to as a diaphragm that aids in respiration. The diaphragm is a sheet of muscle that is arranged with respect to the upper Gastrointestinal (GI) tract (e.g., the UES, esophagus, LES, and portion of pharynx and stomach) to create a pressure inversion point (PIP) or respiratory inversion point (RIP). At the PIP/RIP, pressure associate with respiration inverts such that, above the PIP, pressure decreases during inhalation and increases during exhalation and, below the PIP, pressure increases during inhalation and decreases during exhalation. This muscle also helps to regulate reflux of stomach material into the esophagus.

Manometry is a measurement or evaluation of pressure. Esophageal manometry is a test to measure motor function or muscular pressure along the upper GI tract. Esophageal manometry is used to evaluate the contraction function of the upper GI tract in many situations (e.g., breathing, swallowing food, swallowing liquid, drinking, coughing, etc.) and can be useful for diagnosing symptoms that originate in the esophagus, for example, difficulty in swallowing food or liquid, heartburn, and chest pain to determine the cause of the symptoms, for example, dysphasia or achalasia.

A variety of esophageal manometry systems have been used to study pressure along the upper GI tract. Such systems typically include a catheter or other probe that is inserted into the upper GI tract via the nose and guided into the stomach. One or more pressure sensors arranged with respect to the probe (e.g., internal, external, etc.) detect pressure from different positions within the upper GI tract as the probe is withdrawn. Each sensor transmits its detected values out of the catheter using an electronic or optical signal.

Typically, patients with a swallowing problem such as dysphagia initially undergo an upper endoscopy to investigate the possibility of a mechanical obstruction (e.g., a tumor and/or other physical structure blocking the esophagus). If a result of the endoscopy is negative, the patient is scheduled for an esophageal manometry at a later time when the procedure is available and the patient is not sedated.

Figure 1:
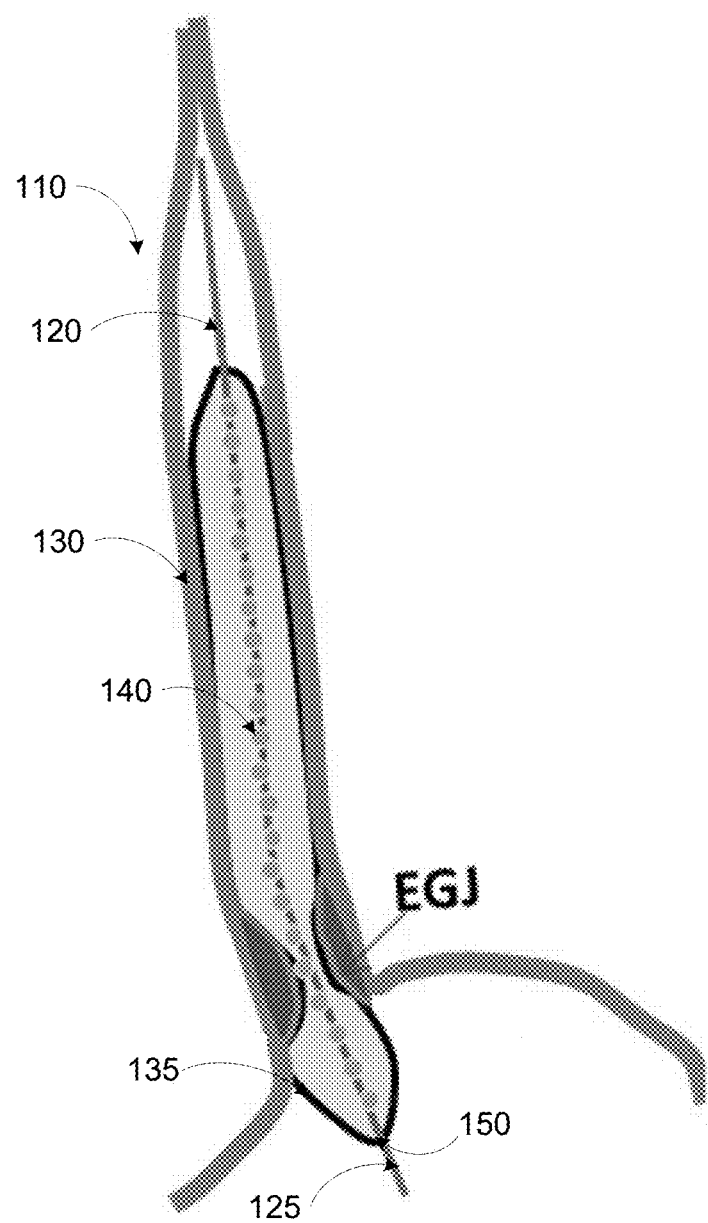
FIG. 1 illustrates an example functional lumen imaging probe (FLIP).

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EMBODIMENTS

I. Brief Description

Certain examples provide methods and systems facilitating an improvement in esophageal function testing and an adjunct for endoscopy.

Certain examples provide a method referred to as panometry using a device that can be used as part of an initial assessment for someone who comes in with dysphasia (e.g., having a problem swallowing, something stuck in the throat, regurgitation, etc.). Rather than the traditional process of first sending the patient for an endoscopy to rule out tumor, obstruction, etc., followed by, if there is non-obstructive dysphasia, scheduling the patient for esophageal manometry (in which a tube is placed through the nose while the patient awake and they swallow and pressure is recorded through the nose catheter), panometry can replace manometry and be conducted during the initial endoscopy rather than as a separate follow-up procedure.

Using manometry, the patient swallows fluids (e.g., 10 swallows). In contrast, using panometry, a balloon is inflated in the esophagus to create the same effect generated by swallowing water without having the patient swallow water or other fluid. The inflated balloon causes a physical reaction by conforming to the available space in the esophagus. Balloon distension and physiological response to the distention can be used to define disease entities. Because the balloon is bigger than swallowing a small glass of water, conditions can be defined with a higher degree of sensitivity than existing techniques. Thus, panometry is faster, more convenient, and more accurate.

Sensors provide data from the balloon distention and are received by a processor and associated application to analyze the data. Such analysis is impractical or impossible if done manually by a human user. Diameters over time are analyzed and topographies are formed. Changes in cross-sectional area can be used to examine peristalsis, etc. Contractions generated through distention correspond to peristalsis.

Additionally, panometry, as opposed to manometry, can provide information regarding opening diameters and other dimensions in the esophagus. Using dimensions and area, pressure(s), diameter(s), and pattern(s) of what's causing the pressures at different points in the esophagus are determined in panometry. Rather than looking purely at measurement of pressure, as in manometry, panometry examines the shape of the esophagus over time. In certain examples, as disclosed herein, esophageal panometry can also include pressure sensors to examine a pressure drop across a trans-esophageal-gastric junction to determine a pressure gradient in addition to dimension and change in dimension in the esophagus.

Although the following discloses example methods, systems, articles of manufacture, and apparatus including, among other components, software executed on hardware, it should be noted that such methods and apparatus are merely illustrative and should not be considered as limiting. For example, it is contemplated that any or all of these hardware and software components can be embodied exclusively in hardware, exclusively in software, exclusively in firmware, or in any combination of hardware, software, and/or firmware. Accordingly, while the following describes example methods, systems, articles of manufacture, and apparatus, the examples provided are not the only way to implement such methods, systems, articles of manufacture, and apparatus.

When any of the appended claims are read to cover a purely software and/or firmware implementation, in at least one example, at least one of the elements is hereby expressly defined to include a tangible medium such as a memory, DVD, Blu-ray, CD, etc. storing the software and/or firmware.

As used herein, the term tangible computer readable medium is expressly defined to include any type of computer readable storage and to exclude propagating signals. As used herein, the term non-transitory computer readable medium is expressly defined to include any type of computer readable medium and to exclude propagating signals.

Certain examples provide systems and methods to implement Esophageal Panometry. Esophageal panometry is a unique approach to processing and displaying data obtained using a device that can be modified to provide a more comprehensive evaluation of esophageal function. The device, referred to herein as a Functional Lumen Imaging Probe (FLIP), obtains simultaneous cross sectional area measurements of the esophagus using an impedance planimetry technique. Sensor(s) are arranged along a catheter or probe that fills with saline and can display a geometry of an esophageal lumen and provide measure(s) of pressure. The FLIP device measures compliance of the esophageal wall and/or lower esophageal sphincter. The FLIP device is used as an intraoperative tool, for example.

For example, the FLIP device (e.g., EndoFLIP® by Crospon, Inc., of Carlsbad, Calif.) uses impedance planimetry (IP) to characterize a geometry of a measurement area (e.g., an esophageal measurement area). Impedance planimetry uses alternating current (AC) voltage measurements made between pairs of electrodes to estimate an extent of a diameter of a medium (a conductive fluid) at a mid-point between those electrodes. The measurements can be obtained provided the voltage drop across the medium is generated from a constant AC current source and the conductivity of the medium is constant and known for a given temperature.

In certain examples, voltage probes are separated by a fixed distance (L) and are connected via wires to a voltage meter. A constant current source is applied, and an electric field is generated in a conductive medium contained in a balloon constrained by walls of a body lumen. Resistance (R) or impedance can be determined by:

$$V/I = R = \frac{L}{A\sigma} = \frac{L}{\Pi(Dest/2)^2 \cdot \sigma}. \quad \text{(Eq. 1)}$$

As used in Equation 1, R, a resistance (impedance) given by V/I, can be calculated as the AC current (I) is known and is fixed, and the AC voltage (V) is measured across the pair of electrodes. If L is a fixed distance between the electrodes, and the medium conductivity ($\sigma$) is known for a given temperature, then Dest can be determined. An estimate of the balloon or cylinder diameter (Dest) at a given electrode position is derived from the measured cylinder area (A) using an assumption that the balloon is symmetrical about its longitudinal axis at that electrode position.

Equation 1 shows that V is inversely proportional to $Dest^2$; therefore, the diameter can be estimated based on the voltage reading. If the conductive medium is contained in a flexible balloon and an array of voltage electrodes used, the shape of the balloon can be reproduced based on the voltage readings. This is the basis of the FLIP imaging technique.

Certain examples inject a specially-formulated conductive solution into a balloon catheter placed in the measurement area. The balloon includes an array of electrodes that measure voltage. The FLIP system (e.g., the EndoFLIP® System) uses these voltages to estimate the diameter at a plurality of points (e.g., up to 16 points) along the measurement area. The FLIP system allows snapshots of this data to be saved and commented for reference.

In certain examples, data derived from the FLIP tool are used with a new data display approach and analysis method to measure esophageal peristalsis (e.g., muscle contractile activity) similar to what is usually obtained with esophageal manometry. With certain examples, contractile patterns can be defined to diagnose esophageal diseases, and, in certain examples, additional pressure sensors can be added to the FLIP device to further refine the diagnosis process.

Using systems, apparatus, and methods disclosed and described herein, certain examples facilitate endoscopic evaluation of dysphagia and classification of esophageal motor diseases. Certain examples help assess opening dimensions of the esophagogastric junction during peristalsis. In certain examples, a biomarker for eosinophilic esophagitis can be identified.

In certain examples, a FLIP allows mechanical competence of the gastroesophageal junction (GEJ) to be assessed directly. Specifically, using a distensibility graph, certain examples assess how wide the GEJ opens for a given distension pressure. Distensibility of the wall of the esophagus changes (e.g., reduces) in patients with Eosiniphilic Esophagitis (EoE). By monitoring esophageal wall distensibility, a FLIP system can be used as a tool both to assist in diagnosis of EoE and to track the treatment progress of patients.

Certain examples provide a completely new technique to assess esophageal function by assessing a response of muscle activity to esophageal distension. Using systems, apparatus, and methods disclosed and described herein, no transnasal intubation is required, resulting in improved acceptance and tolerability, for example. Esophageal panometry can be performed while the patient is sedated resulting in improved acceptance and tolerability, for example. Certain examples help provide a cost saving and time saving due to a reduction in utilization of manometry.

Certain examples provide an application and refinement of high resolution impedance planimetry combined with axial manometry that utilizes bolus distention to define both mechanics and mobility of the esophagus. Certain examples utilize a new conceptual model for analysis that both categories esophageal motility and assess esophagogastric junction (EGJ) opening dimensions with pressure gradients using FLIP topography. The conceptual model utilizes bolus distention rather than swallow-triggered activity. The conceptual model can define peristalsis based on luminal cross-sectional area (CSA) changes similar to fluoroscopy, for example. The conceptual model can define an optimal pressure gradient to open the EGJ, for example. The conceptual model can define distensibility of the esophagus and plot data based on a distensibility index and distensibility plateau.

In certain examples, a FLIP measures luminal cross-sectional area and pressure during controlled volumetric distension. By applying a developed software program to produce FLIP topography plots, organized, contractile activity in response to controlled distension can be visualized and analyzed. Contractile thresholds and characteristics for distension-induced esophageal body contractile activity can be described using FLIP topography in normal controls, for example.

FIG. 1 illustrates an example functional lumen imaging probe (FLIP) 110. The example FLIP 110 includes a catheter 120 and an infinitely compliant bag 130 mounted on a distal end 125 of the catheter 120. The bag 130 houses a plurality of ring electrodes 140 spaced throughout the bag 130 along the catheter 120, and a solid-state pressure transducer 150 positioned at a distal end 135 of the bag 130. The bag 130 can be tapered at both ends to form a cylindrical shape at a center of the bag 130, for example.

In certain examples, the FLIP assembly 110 forms a high-resolution impedance planimetry segment (e.g., 8-cm, 16-cm long, etc.) that can be positioned with the distal end 125 across a patient's esophagogastric junction (EGJ) during endoscopy. Simultaneous (or substantially simultaneous including some positioning, transmission, and/or processing delay) diameter and intra-bag pressure measurements can be obtained during stepwise bag distensions (e.g., from 5-60 ml, etc.) and exported (e.g., to a specialized MATLAB™ program, etc.) to generate FLIP topography plots. Distension volume and pressure thresholds can be identified for a start of esophageal contractions (reactivity) and for an onset of repetitive antegrade contractions (RACs), which likely represent secondary peristalsis, for example. Contraction duration, interval, magnitude, velocity, and associated pressure-changes can be measured above the EGJ (e.g., at 8 and 3-cm, etc.) during RACs. Thus, distension-induced esophageal contractions can be assessed utilizing FLIP topography. Incorporation of FLIP provides an adjunctive tool for esophageal distensibility and motility assessment.

Figure 2:
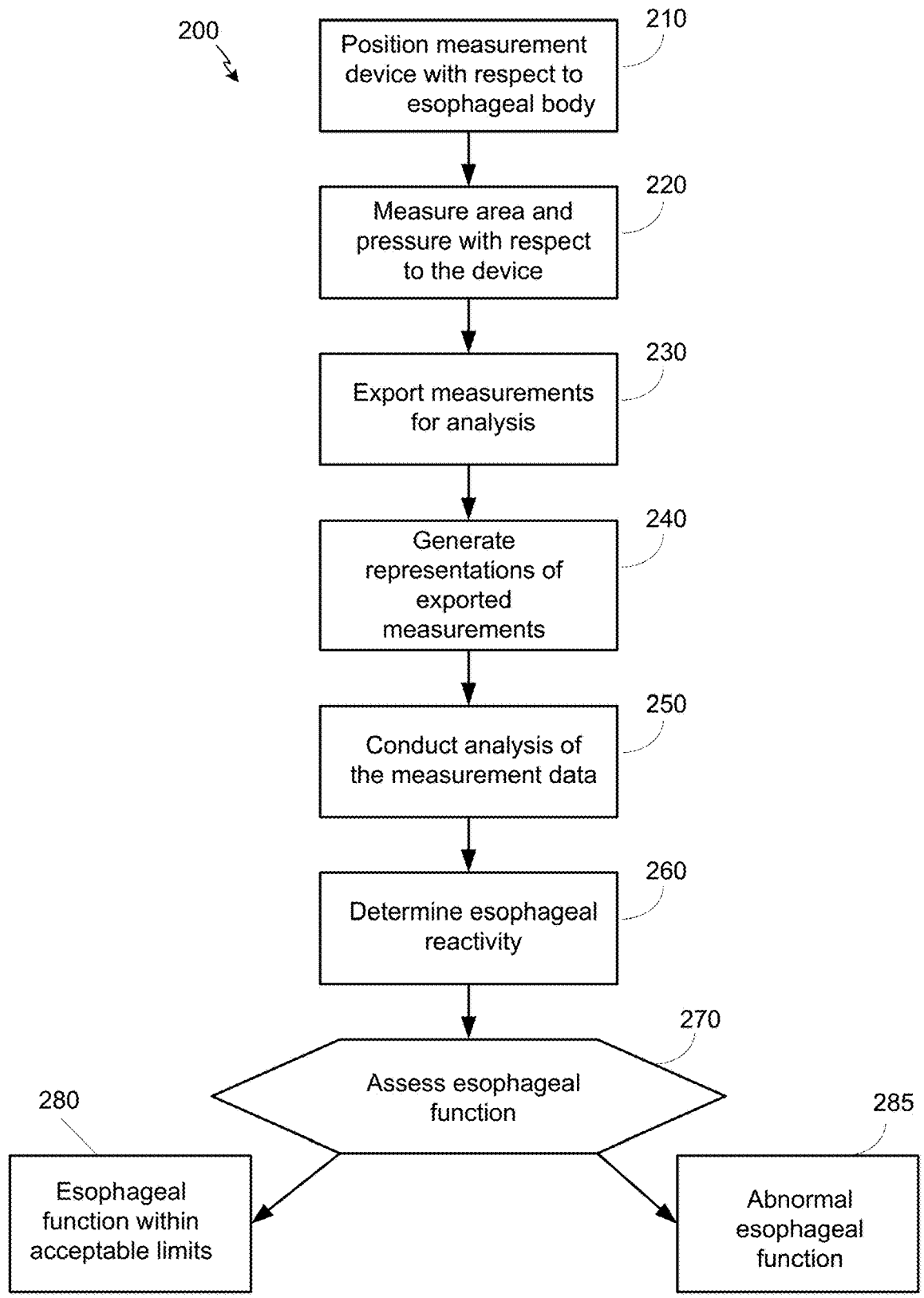
FIG. 2 illustrates a flow diagram of an example method for assessment of esophageal function.

FIG. 2 illustrates a flow diagram of an example method 200 for assessment of esophageal function using a functional lumen imaging probe (e.g., the example FLIP 110). The FLIP is a novel tool for the assessment of esophageal function. By utilizing multiple closely-spaced impedance planimetry channels within a balloon (e.g., balloon or bag 130), the FLIP measures simultaneous luminal cross-sectional areas along the length of the measurement segment during controlled volumetric distension. When combined with measurement of the intra-bag pressure, the distensibility can be measured. Within the esophagus, the FLIP can be used to evaluate the distensibility of the esophagogastric junction (EGJ) and direct treatment in patients with achalasia. Demonstration of abnormal distensibility of the esophageal body utilizing the FLIP in patients with eosinophilic esophagitis can also provide an ability to prognosticate risk of food impaction or need for dilation therapy. An elongated (e.g., 16-cm balloon) FLIP can allow simultaneous evaluation of the EGJ and the distal esophageal body, for example.

At block 210, a measurement device, such as a FLIP (e.g., example FLIP 110) or other probe, is positioned with its distal end across the EGJ and inflated.

In an example, the FLIP assembly 110 can include a 240-cm long, 3-mm outer diameter catheter 120 with an infinitely compliant bag 130 (e.g., up to a distension volume of 60 mL) mounted on the distal 18 cm 125 of the catheter 120. The bag 130 houses 17 ring electrodes 140 spaced 1 cm apart and a solid-state pressure transducer 150 positioned at the distal end 135 of the bag 130 to provide simultaneous measurement of 16 channels of cross-sectional area (CSA) and intra-bag pressure. The bag 130 can be tapered at both ends to assume a 16-cm long cylindrical shape in the center of the bag 130 that forms an impedance planimetry segment. The impedance planimetry segment had a minimum-to-maximum range of measureable CSA within the infinitely compliant range of 21-380 mm$^2$; assuming the lumen cross-sections are circular, this corresponds to a diameter of 5.2-22 mm. Values above 380 mm$^2$ (22-mm diameter) can be measured, but mechanical properties of the bag may be engaged above this distension range. Measurements from the impedance planimetry electrode pairs and the pressure transducer are sampled at 10 Hz, for example, with a data acquisition system and transmitted to a recording unit.

Figure 3:
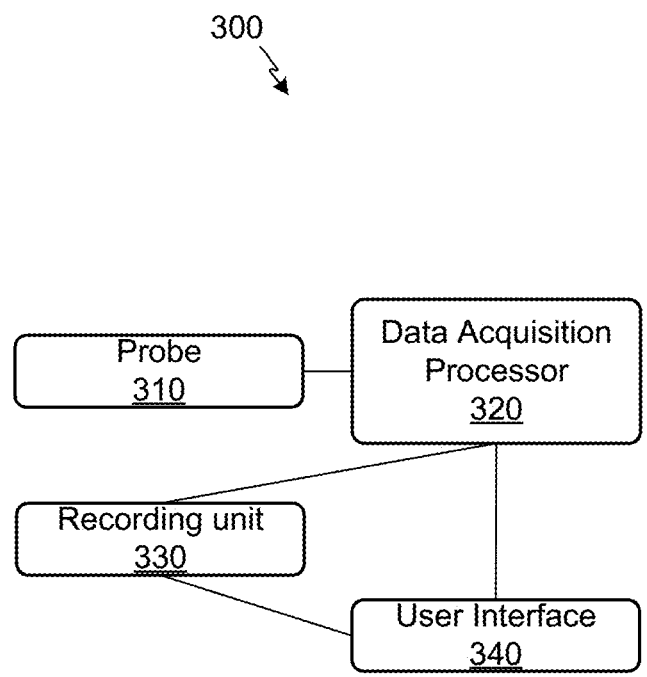
FIG. 3 illustrates an example data acquisition system.

FIG. 3 illustrates an example data acquisition system 300 including a probe 310, a data acquisition processor 320, and a recording unit 330. The probe 310 is positioned with respect to a target esophagus and transmits data to the data acquisition processor 320. The data can be analyzed by the data acquisition processor 320 and recorded via the recording unit 330. Results can be displayed, control can be facilitated, parameters can be adjusted, etc., via a user interface 340 communicating with the data acquisition processor 320 and the recording unit 330, for example.

In certain examples, the probe is placed transorally and positioned with the distal 1-3 impedance sensors beyond the EGJ. The probe can be positioned using an endoscope that is then withdrawn before measurement, for example.

The positioned probe is inflated to create a test condition that artificially triggers a behavior in the esophagus that can identify a disease or condition, for example.

At block 220, CSA and intra-bag pressure are measured. CSA and intra-bag pressures can be measured simultaneously (or substantially simultaneously), for example.

Continuing the above example, simultaneous CSAs and intra-bag pressures can be measured during 5 ml step-wise distensions beginning with 5 ml and increasing to 60 ml. In the example, each step-wise distension is maintained for 5-20 seconds. The recording unit (e.g., recording unit 330) can be configured to stop infusing and display an alarm message if the intra-bag pressure exceeds 60 mmHg to avoid unintended dilation.

At block 230, measurements (e.g., CSA and intra-bag pressure measurements) that have been obtained from sensors in the probe are exported for analysis. For example, CSA and pressure data can be exported to the data acquisition processor 320 and recording unit 330 for storage and analysis.

At block 240, representations of the measurements are generated based on the sensor data. For example, incorporation of the multiple impedance planimetry channels output, essentially high-resolution impedance planimetry, to a specialized program (e.g., a MATLAB™ application) generates FLIP topography plots that allow representation of space-time luminal diameter changes occurring during the FLIP distension protocol.

At block 250, analysis of the measurement data is conducted to identify threshold and onset conditions. For example, observations of esophageal contractions in response to distension (sometimes termed reactivity) during impedance planimetry assessment of the esophageal body can be identified. Essential functions of the esophagus are to accommodate to and clear contents introduced to the esophagus. Clearance of residual (e.g., remaining contents after swallow-induced, primary, peristalsis) or refluxed esophageal contents often occurs by distension-induced (secondary) peristalsis. As the FLIP measures simultaneous luminal diameters and pressure during controlled distension, the probe is uniquely suited to evaluate the esophageal response to distension, including distension-induced esophageal contractions and motility.

Thus, features of esophageal contractions during volumetric distension can be described in a cohort of asymptomatic, healthy controls utilizing FLIP topography. Additionally, potential metrics of distension-induced esophageal contractions can be identified and normative values produced.

Continuing the above example, data including distension volume, intra-bag pressure, and 16 channels of CSA measurements (e.g., via impedance planimetry) over the entire study periods for each subject can be exported to an analysis and/or simulation program such MATLAB™ (by The Math Works, Natick, Mass., USA) for further analysis. Tracings of each channel's measured luminal diameter can be electronically generated with corresponding volume distension and intra-bag pressure by time, for example (see, e.g., FIG. 7A). A topography plot of the interpolated luminal diameters can also be electronically generated, for example (see, e.g., FIG. 7B). Additionally, computer analysis can identify an EGJ-midline by searching for the minimal CSA of the distal six impedance planimetry channels.

In an example, esophageal contractions can be identified by a transient decrease of ≥5 mm in the measured luminal diameter detected in ≥2 consecutive axial impedance planimetry channels. A cutoff of 5 mm, for example, can be utilized to avoid measurement of vascular and respiratory fluctuations. Esophageal contractions can be identified by visualization of the FLIP topography plot and 16 channel diameter tracing output and can be described in terms of propagation direction (e.g., antegrade or retrograde), for example. Contractions can be considered repetitive when ≥3 occur consecutively. Repetitive, antegrade contractions (RACs) are specifically identified as they likely represent distension-mediated (secondary) peristalsis. Esophageal reactivity is defined as any esophageal contractile activity that occurs during the distension protocol. Presence or absence of reactivity and RACs, as well as RAC cessation, are recorded as dichotomous variables. Distension volume and intra-bag pressure are measured at the start of esophageal reactivity, and at the onset and after cessation of RACs, for example.

Figure 7A:
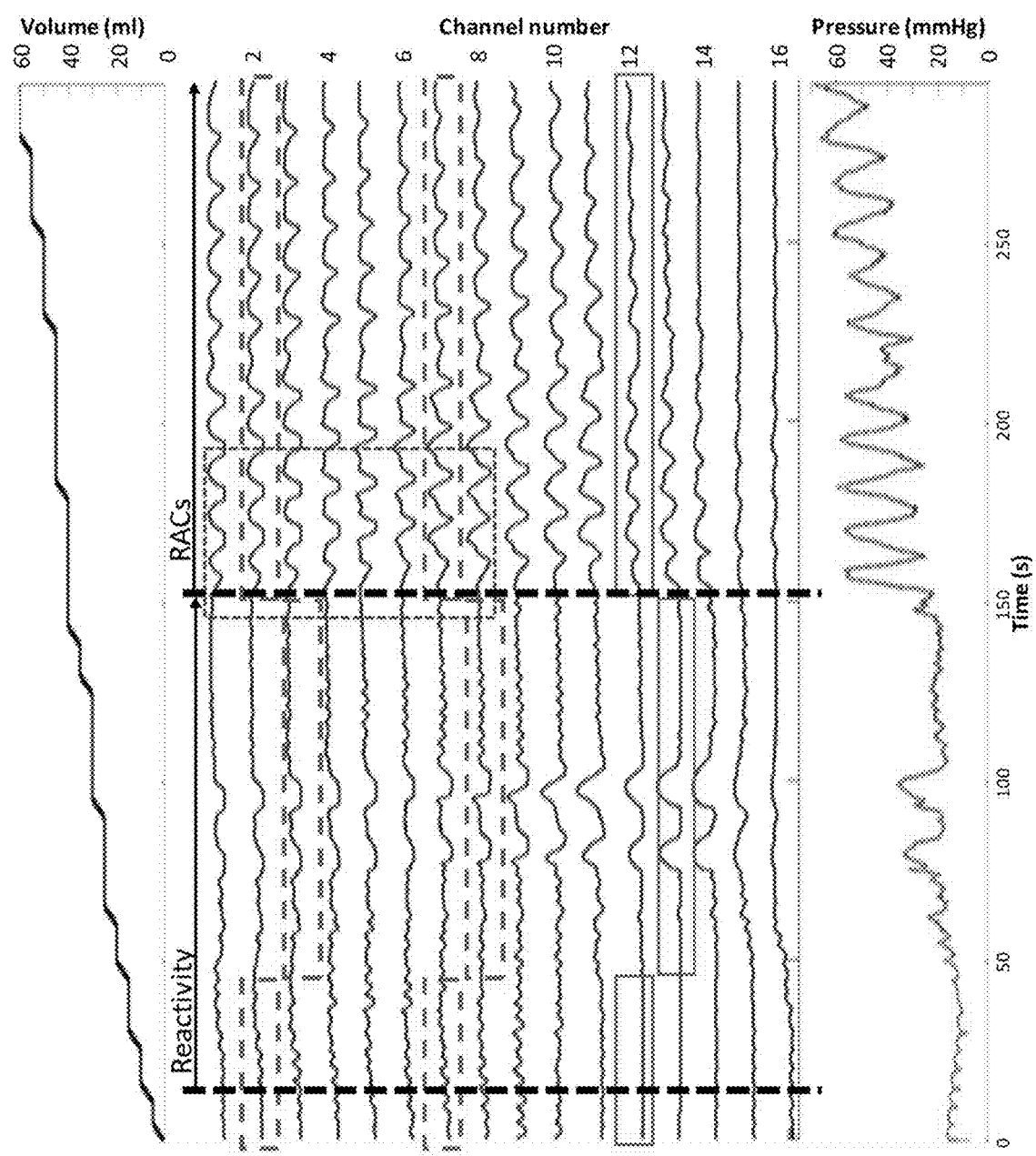
FIGS. 7A-7D illustrate examples of endoscopy panometry measurement data and associated analysis.
Figure 7B:
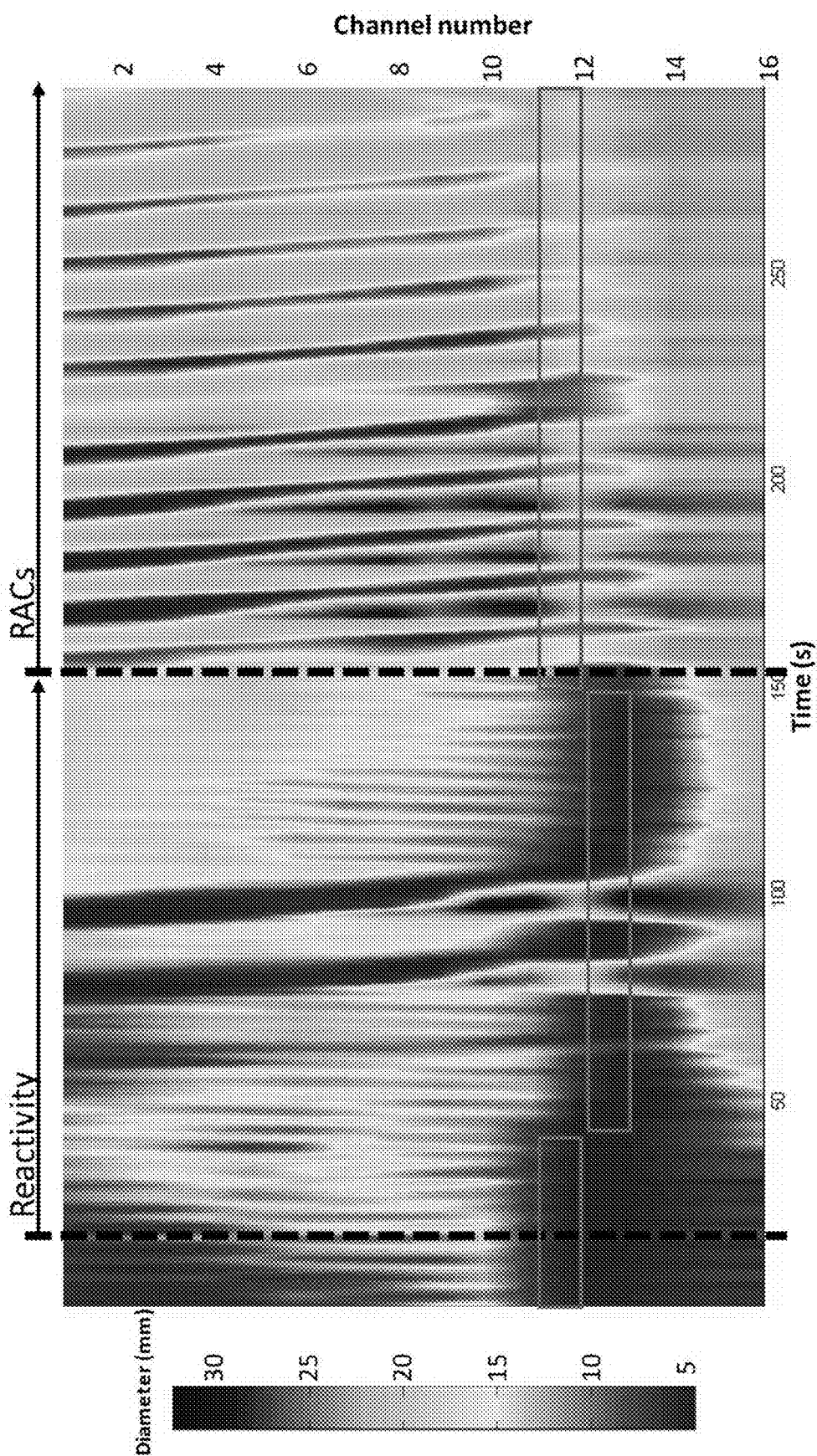
Figure 7C:
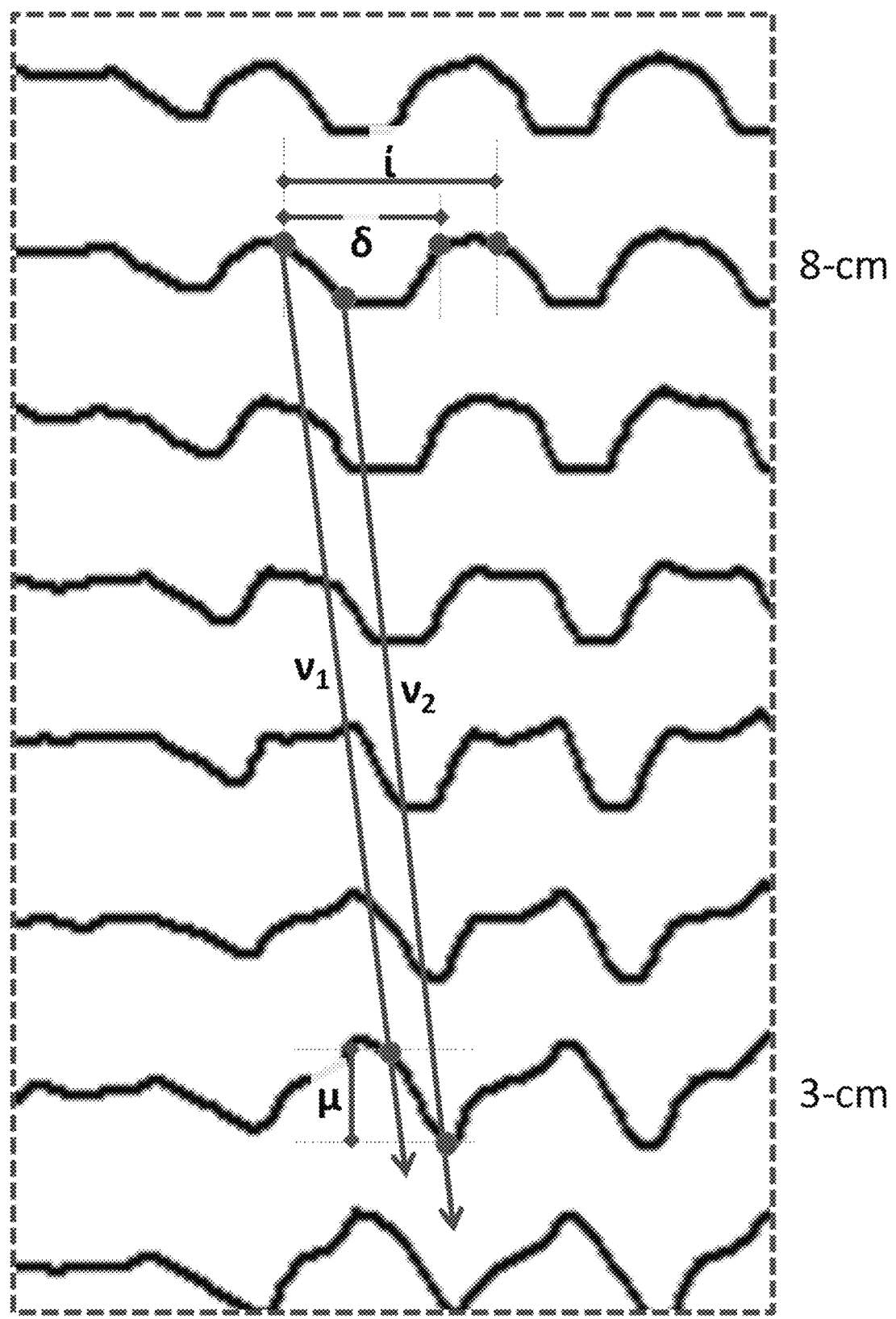
Figure 7D:
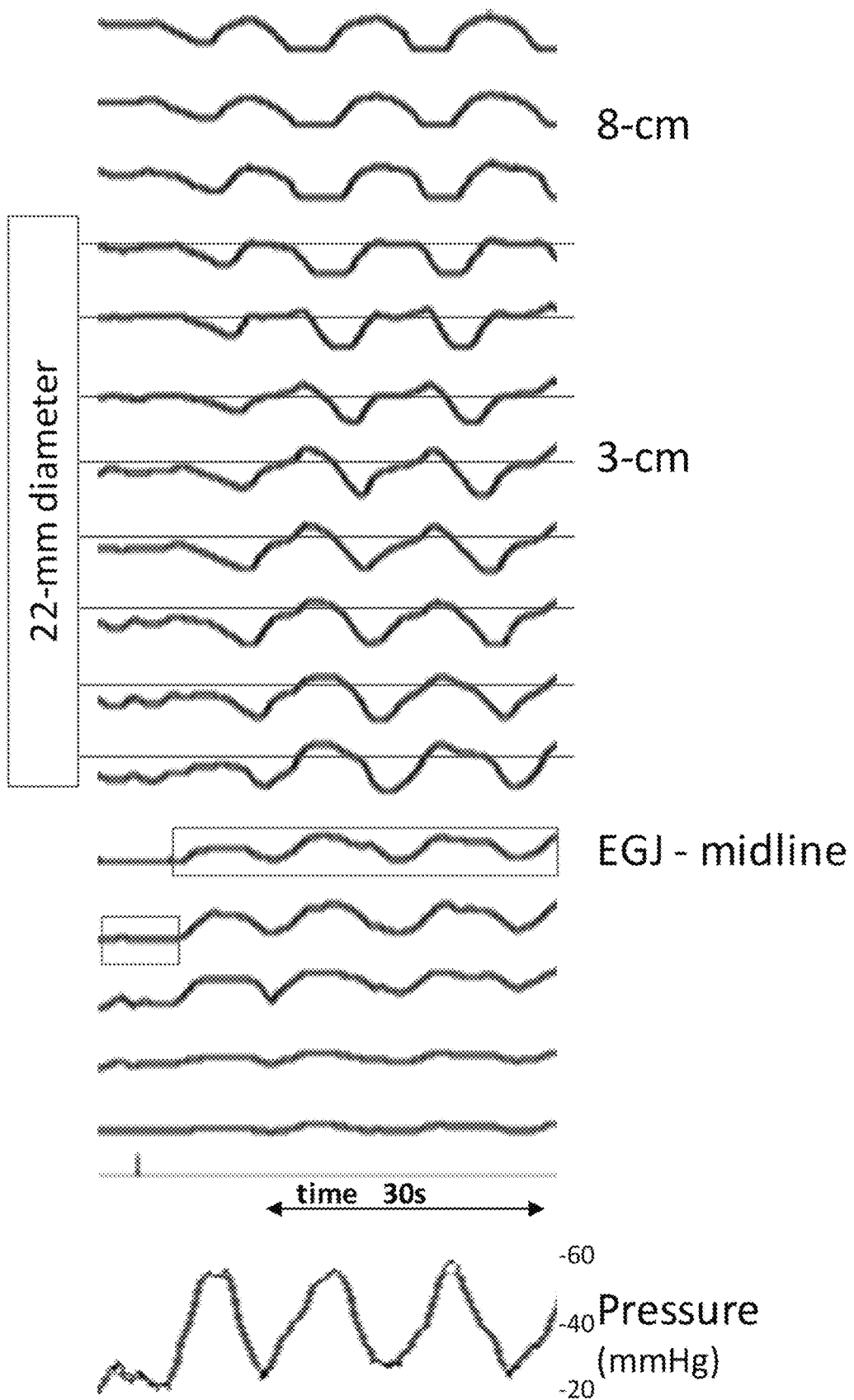

Esophageal contractions during RACs can be further analyzed at 5 and 10 impedance planimetry channels above the EGJ-midline (to correspond with 3 and 8-cm above the proximal border of the EGJ) with measurements of contraction duration, interval, and magnitude, as illustrated, for example, in FIG. 7C. Additionally, contraction wave velocities can be measured using a slope of lines both from a start of contractions ($v_1$) and from nadir diameters ($v_2$) (FIG. 7C). Further, a contraction-associated change in intra-bag pressure can be measured as a difference in nadir and peak pressure associated with a contraction (FIG. 7D). These metrics are applied to the first five RACs (initial RACs) and if present, to RACs continuing after a time of bag distension to 50 ml (late RACs).

In an example analysis, results are expressed as median and interquartile range (IQR). Statistical comparisons can be made within subjects using, for example, the Wilcoxon signed ranks test. Contraction parameters are compared within subjects between proximal and distal measurement segments (e.g., measurements at 8 and 3 cm proximal to the EGJ). To assess for contraction parameter changes during the course of the distension protocol, intra-subject comparison can also be made between the initial and late RACs. In an example analysis, measures can be considered statistically different at a two-tailed p-value <0.05.

At block 260, esophageal reactivity is determined. For example, using the analysis of measurement data, esophageal reactivity to distension can be observed.

Table 1 shows example contraction characteristics for median IQR values when metrics are applied to an example set of RACs (e.g., 66 RACs: 39 total contractions within the first five RACs from eight subjects and 27 RACs that occurred after reaching the 50-ml distension volume from six subjects.

TABLE 1

Summary of repetitive antegrade contraction (RAC) metrics.

| | | ALL RACs | | initial RACs | | late RACs | | p (initial vs. late)* |
|---|---|---|---|---|---|---|---|---|
| | location | median | IQR | median | IQR | median | IQR | |
| Duration (s) | 8-cm | 5.4 | 4.9-6.2 | 5.9 | 5.0-6.5 | 5.4 | 4.9-7.3 | 0.043 |
| | 3-cm | 4.9 | 4.2-5.6 | 5 | 4.2-6.2 | 4.6 | 4.3-6.2 | 0.345 |
| | p (8vs 3)* | 0.012 | | 0.021 | | 0.08 | | |
| Interval (s) | 8-cm | 8.7 | 6.3-10.2 | 8.3 | 6.1-9.3 | 9.9 | 8.2-12.0 | 0.225 |
| | 3-cm | 8.6 | 6.8-10 | 8.8 | 6.7-9.9 | 10 | 8.2-11.6 | 0.893 |
| | p (8vs 3)* | 0.262 | | 0.012 | | 0.68 | | |
| Magnitude (mm) | 8-cm | 9.9 | 6.9-12.8 | 10.9 | 6.8-12.8 | 9.4 | 7.7-11.9 | 0.08 |
| | 3-cm | 9.4 | 8.2-11.2 | 11.1 | 8.4-14.2 | 7.9 | 7.0-10.2 | 0.043 |
| | p (8vs 3)* | 0.889 | | 0.208 | | 0.225 | | |
| Velocity1 (cm/s) | | 1.6 | 1.4-2.4 | 1.8 | 1.4-2.4 | 1.5 | 1.1-1.7 | 0.138 |
| Velocity2 (cm/s) | | 2 | 1.7-4 | 1.9 | 1.4-4.0 | 1.8 | 1.5-2.4 | 0.225 |
| Pressure change (mmHg) | | 20.8 | 7.9-22.7 | 18.4 | 6.0-22.2 | 22.6 | 18.4-28.1 | 0.225 |

IQR—interquartile range.
*Wicoxon signed ranks test.

In the example above, when comparing metrics from 8 and 3 cm above the EGJ, the contractions were longer in median duration at 8-cm than 3-cm and similar in median contraction magnitude. The interval between contractions is statistically similar between 8 and 3 cm above the EGJ in all contractions, but within only the first five RACs, there was a statistical difference such that the interval between the contractions at 8 cm [8.3-s (6.1-9.3)] was shorter than the contraction interval at 3-cm [8.8-s (6.7-9.9); p=0.012].

To assess for changes in metrics during the course of the distension protocol, metrics of initial RACs and late RACs can be compared (Table 1). In the six subjects of the example that exhibited RACs after reaching a 50-ml distension volume, the initial five RACs are present until reaching distension volumes ranging from 35-45 ml. Comparison of initial RACs and late RACs demonstrates a decrease in contraction duration later in the distension protocol at 8-cm above the EGJ, but not at 3-cm above the EGJ. In the example, the contraction interval remains stable throughout the distension protocol. There is also a decrease in the contraction magnitude during the distension protocol at both 8-cm and at 3-cm above the EGJ. The contraction velocities, both from the start of contraction and from the nadir diameter, appear to remain stable throughout the distension protocol.

In the example, intra-bag pressure changes associated with RACs are a median 20.8 mmHg, IQR 7.9-22.7. Comparison of pressure changes associated with initial RACs (18.4 mmHg, 6.0-22.2) and late RACs (22.6, 18.4-28.1) does not demonstrate a significant difference (p=0.225). Timing of the pressure changes relative to regional contraction is depicted, for example, in FIG. 7D. The bag diameter is observed to increase above 22-mm (a diameter limit below which the bag compliance is infinite) in six of the eight subjects with RACs; thus pressure changes observed in these subjects likely represent some contribution of the bag properties.

Thus, using the FLIP with a 16-cm length balloon spanning the distal esophageal body and EGJ in normal controls and incorporating a specialized program to generate FLIP topography plots, organized, propagating contractile activity can be observed in the esophageal body during graded esophageal distension. The majority of subjects demonstrated RACs during the protocol, and the majority of these subjects' RACs continued through the entire distension protocol. Initial normative values of thresholds for distension-induced esophageal reactivity and RACs can be generated as well as RAC-related metrics including contraction duration, magnitude, and interval. Also, changes in contraction duration and magnitude occur during the distension protocol such that the proximal contraction duration is shorter and the contraction magnitudes (at both measurement channels) are smaller at higher distension volumes.

At block 270, based on esophageal reactivity, esophageal function is assessed. For example, an analysis of CSA and pressure measurements and resulting esophageal reactivity and comparison to threshold(s) can be used to determine whether evaluated esophageal function falls within acceptable limits or is determined to be abnormal.

In certain examples, esophageal reactivity or oscillation can be examined as a trigger point of reactivity to volume/pressure activity. Such oscillatory behavior of the esophagus may vary based on disease and may determine or impact disease typing and choice of surgery and/or other treatment. For example, an onset of oscillation and magnitude of oscillation.

Based on the assessment, esophageal function is determined to be within acceptable limits (e.g., values falling within "normal" or accepted thresholds) or abnormal. At block 280, a determination that esophageal function is within acceptable limits is provided (e.g., via a user interface to a user). At block 285, a determination of abnormal esophageal function is provided (e.g., via a user interface to a user). The determination of abnormal esophageal function can be used to determine follow-up examination and procedure, for example.

Thus, peristaltic assessment can be facilitated using a probe, such as a FLIP. A pressure sensor located at the distal end of the probe bag can be placed distal to the EGJ. Intra-bag pressure measurements can be transmitted during times of EGJ opening, either directly due to luminal distension or associated with esophageal contraction, as well as additional time-point-specific pressure assessment of the esophageal body during lumen obliterating contractions and/or in disease states with abnormal EGJ opening, such as achalasia. The intra-bag pressure changes are temporally associated with varying diameter changes throughout the measurement segment such that the pressure increase can be associated with contraction in the mid-esophageal body and diameter increases in the distal esophageal body.

Furthermore, as the pressure decreases concurrent with increasing diameters at the mid-esophageal body and decreasing diameter in the distal esophagus, this could represent auxotonic relaxation in the mid-esophageal body (which would not be expected) and auxotonic contraction in the distal esophagus (expected) during ampullary emptying; however, the pressure decrease and proximal diameter increase may also represent proximal re-distribution of the intra-bag fluid during the distal esophageal contraction. In certain examples, incorporation of additional pressure sensors distributed within the proximal bag can help clarify these findings and supplement the esophageal physiologic assessment provided by the FLIP. Additionally, increasing the bag diameter (e.g., to 30 mm or more) can help exclude contributions of the bag properties to the measured pressures. Elongating the bag can also allow for a greater extent of the esophageal body to be evaluated, a larger bag size is balanced against patient tolerability for catheter placement.

Additionally, in certain examples, incorporation of a swallow-detection device, such as surface electromyography (EMG) sensors, can help to distinguish swallow-induced from distension-induced contractile events. Further, prolongation of the protocol time at a stable distension volume beyond the 20-30 seconds used in certain examples described above can help provide a more consistent measure of contraction parameters and help avoid potential changes observed at higher distension volumes. While, in certain examples, FLIP placement occurs during moderately sedated endoscopy in an attempt to increase subject tolerance, sedation can only be used to facilitate placement rather than for the completion of the distension protocol. Thus, while a slight prolongation of the FLIP study distension protocol may add a small amount (e.g., 5-10 minutes) to procedure time, it is unlikely to increase sedation dosages.

Application of FLIP topography represents a novel method for assessment of esophageal function in response to distension. In addition to providing methods and systems for assessment of esophageal sphincter and wall distensibility, it allows for assessing presence and induction thresholds of distension-induced peristalsis, which can potentially have diagnostic and/or therapeutic potential. The manometric assessed peristaltic response to esophageal air infusion, water infusion, and/or balloon distension can differ from normal controls in patients with erosive and non-erosive reflux disease and patients with non-obstructive dysphagia. Additionally, distension thresholds can be altered by several pharmacologic agents, including topical lidocaine, baclofen (a GABA-agonist), and mosapride (a 5-HT4 agonist). Additionally, erythromycin (e.g., a motilin agonist) may increase contraction frequency and magnitude of secondary peristalsis (but not primary peristalsis) and butylscopolamine (an anticholinergic agent) may decrease contraction frequency and magnitude in secondary peristalsis. Thus, the peristaltic response to esophageal distension can have some clinical implications and can be assessed via FLIP topography.

Thus, the presently disclosed FLIP topography methodology and technology facilitates improved esophageal function assessment. Certain examples provide an ability to simultaneously assess distensibility of the esophageal body and lower sphincter and distension-induced contractile and peristaltic activity. This technique could be incorporated into an endoscopic assessment of dysphagia when no overt obstruction is identified on endoscopy with minimal inconvenience to the patient.

As disclosed and described herein, esophageal panometry provides an application and refinement of high-resolution impedance planimetry combined with axial manometry that utilizes bolus distention to define both mechanics and motility of the esophagus. Rather than swallow-triggered activity, bolus distention from a probe bag/balloon is utilized to identify an abnormality. Information is visualized using FLIP topography with customized balloon positioned through the EGJ and an associated algorithm that identifies the EGJ. As a result, peristalsis can be defined based on luminal CSA changes similar to fluoroscopy, and an optimal pressure gradient to open the EGJ can be defined. Further, distensibility of the esophagus can be defined, and data can be plotted based on distensibility index and distensibility plateau, for example.

Reactivity of the esophageal wall to volumetric distention can be assessed with the FLIP device and can discern different patterns of activity (e.g., reactivity versus peristalsis). A pattern of reactivity to fixed balloon distention in normal controls is predictable, but does have some variability. Disease States may have different trigger points for reactivity and this could have clinical significance in terms of bolus clearance. For example, loss of reactivity in achalasia may exacerbate bolus retention, and an inability to trigger peristalsis may predispose to worsening GERD and post-operative dysphagia.

Figure 4:
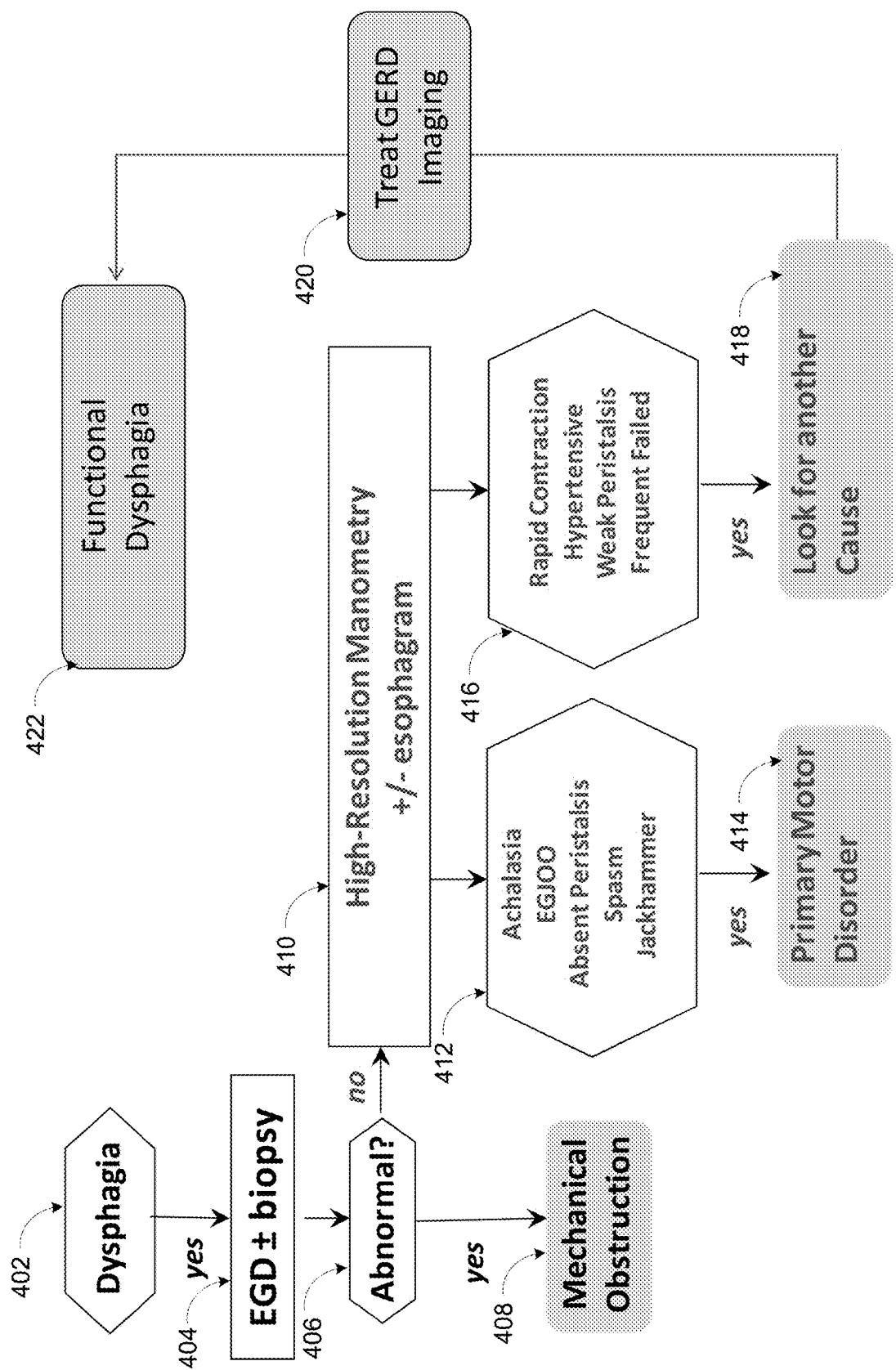
FIG. 4 illustrates a traditional method or paradigm for examining a patient with dysphagia/food impaction.
Figure 5:
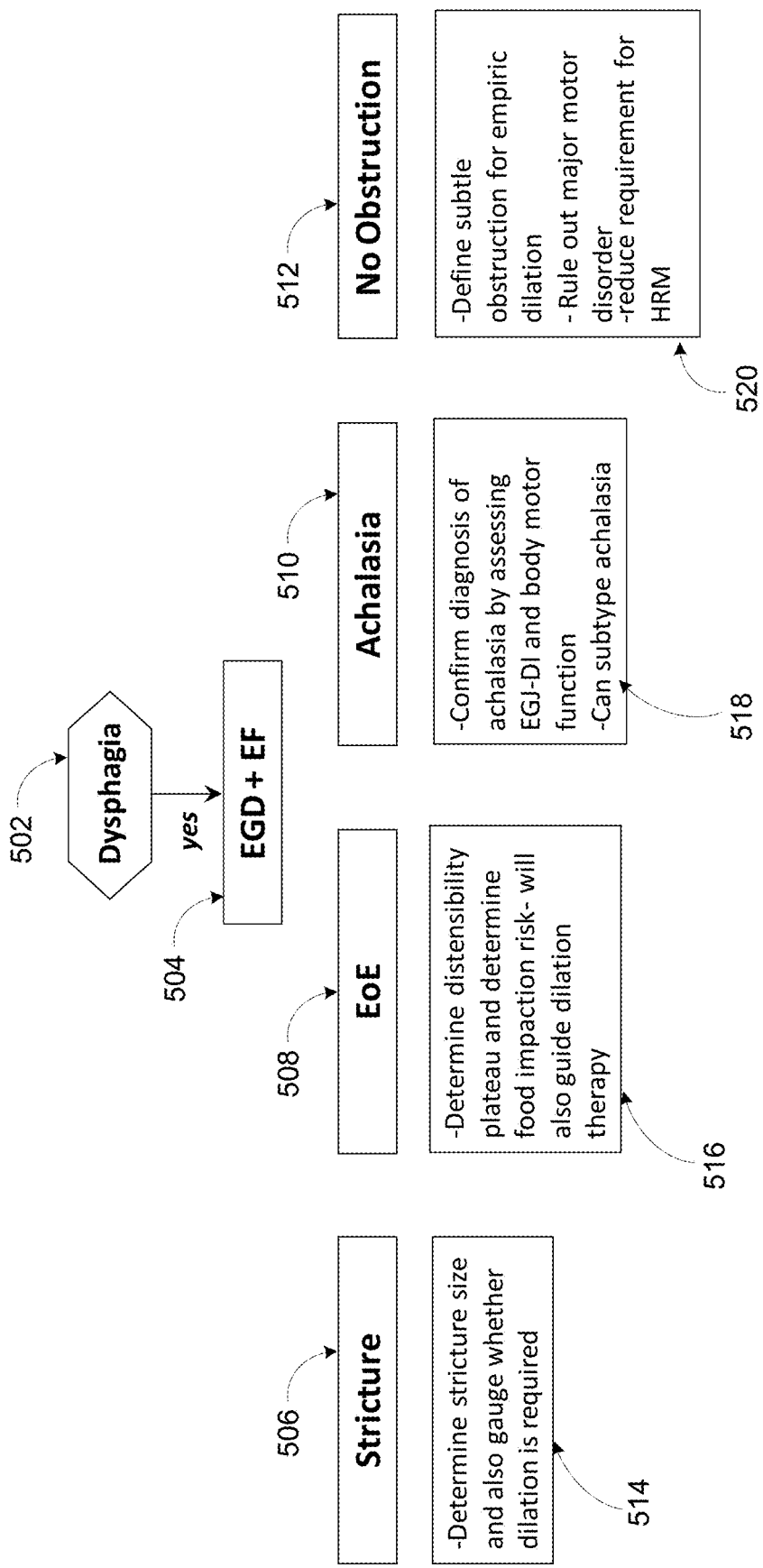
FIG. 5 shows a probe or FLIP-based paradigm for examining a patient with dysphagia/food impaction.

While FIG. 4 illustrates a traditional method or paradigm for examining a patient with dysphagia/food impaction through endoscopy, biopsy, high resolution manometry (with or without esophagram) and potentially GERD imaging, FIG. 5 provides a probe or FLIP-based paradigm as disclosed and described herein. Using endoscopy (EGD) plus probe-based analysis (e.g., EndoFLIP or 'EF'), dysphagia can be analyzed to determine stricture, EoE, achalasia, or no obstruction, for example.

Thus, as shown in FIG. 4, a patient suspected of having dysphagia (402) is examined through endoscopy and biopsy (404) to evaluate whether or not the endoscopy and biopsy are abnormal (406). If the endoscopy and/or biopsy are abnormal, then a mechanical obstruction is identified (408). However, if the endoscopy and biopsy are not abnormal, then a high resolution manometry (alone and/or with an esophagram) is performed (410). If a condition such as achalasia, esophagogastric junction outflow obstruction (EGJOO), absent peristalsis, spasm, jackhammer, etc., is present (412), then a primary motor disorder is diagnosed (414). However, if a condition such as rapid contraction, hypertensive, weak peristalsis, frequent failed, etc., is present (416), then another cause is investigated (418). Then, gastroesophageal reflux disease (GERD) imaging is conducted (420) to identify functional dysphagia (422).

In contrast, as shown in FIG. 5, a patient suspected of dysphagia (502) is examined using endoscopy plus a probe-based analysis (504). Using the EGD plus EF, as described above, dysphagia can be analyzed to determine stricture (506), eosinophilic esophagitis (EoE) (508), achalasia (510), or no obstruction (512), for example. If stricture is identified (506), then stricture size can be determined, as well as gauging whether dilation is required for the stricture (514). If EoE is identified (508), then a distensibility plateau is determined as well as a food impaction risk (516). Determination of distensibility plateau and food impaction risk (516) can also be used to guide dilation therapy, for example. If achalasia is identified (510), then a diagnosis of achalasia is confirmed by assessing esophagogastric junction distensibility (EGJ-DI) and body motor function (518). An assessment of EGJ-DI and body motor function can help to subtype the achalasia (518), for example. If no obstruction is identified (512), then a subtle obstruction can be defined for empiric dilation and major motor disorder can be ruled out (520). Additionally, a requirement for high-resolution manometry (HRM) can be reduced (520).

Figure 6:
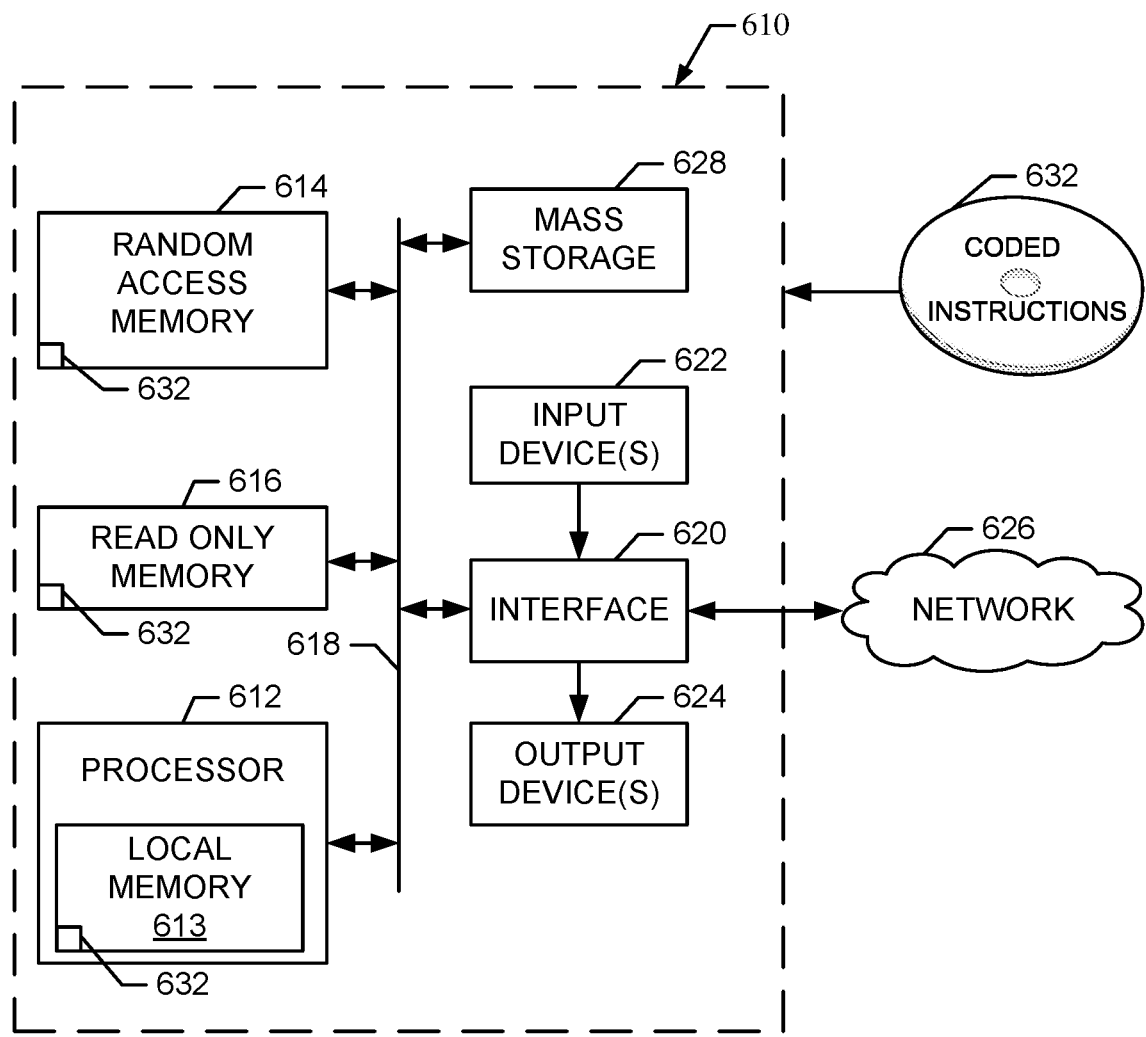
FIG. 6 is a block diagram of an example processor system that may be used to implement systems, apparatus, and methods described herein.

FIG. 6 is a block diagram of an example processor system 610 that may be used to implement systems, apparatus, and methods described herein. As shown in FIG. 6, the processor system 610 includes a processor 612 that is coupled to an interconnection bus 614. The processor 612 may be any suitable processor, processing unit, or microprocessor, for example. Although not shown in FIG. 6, the system 610 may be a multi-processor system and, thus, may include one or more additional processors that are identical or similar to the processor 612 and that are communicatively coupled to the interconnection bus 614.

The processor 612 of FIG. 6 is coupled to a chipset 618, which includes a memory controller 620 and an input/output ("I/O") controller 622. As is well known, a chipset typically provides I/O and memory management functions as well as a plurality of general purpose and/or special purpose registers, timers, etc. that are accessible or used by one or more processors coupled to the chipset 618. The memory controller 620 performs functions that enable the processor 612 (or processors if there are multiple processors) to access a system memory 624 and a mass storage memory 625.

The system memory 624 may include any desired type of volatile and/or non-volatile memory such as, for example, static random access memory (SRAM), dynamic random access memory (DRAM), flash memory, read-only memory (ROM), etc. The mass storage memory 625 may include any desired type of mass storage device including hard disk drives, optical drives, tape storage devices, etc.

The I/O controller 622 performs functions that enable the processor 612 to communicate with peripheral input/output ("I/O") devices 626 and 628 and a network interface 630 via an I/O bus 632. The I/O devices 626 and 628 may be any desired type of I/O device such as, for example, a keyboard, a musical keyboard, a control surface, a video display or monitor, a mouse, etc. The network interface 630 may be, for example, an Ethernet device, an asynchronous transfer mode ("ATM") device, an 802.11 device, a DSL modem, a cable modem, a cellular modem, etc., that enables the processor system 610 to communicate with another processor system.

While the memory controller 620 and the I/O controller 622 are depicted in FIG. 6 as separate blocks within the chipset 618, the functions performed by these blocks may be integrated within a single semiconductor circuit or may be implemented using two or more separate integrated circuits.

FIG. 7A provides an example of FLIP topography. FIG. 7A depicts example distension volume (top), 16-channels of diameter changes (middle), and intra-bag pressure (bottom) over the course of the study protocol in a single subject. FIG. 7B shows a topographic representation of diameter changes using a color scale. The initiation of reactivity and repetitive, antegrade contractions (RACs) are illustrated with vertical dashed lines. In this subject, RACs continue through the end of the study protocol. The identified esophagogastric (EGJ) midline is represented by the solid blue box. Metrics are generated from the channels at 5 and 10 cm above the EGJ midline (dashed-blue boxes). The section within the dashed red box of FIG. 7A is enlarged in FIG. 7C.

FIG. 7C provides an expanded view of example FLIP topography metrics. Metrics in the example are measured at impedance planimetry channels 3 and 8 cm proximal to the EGJ (5 and 10 cm proximal to the EGJ midline). Contraction duration ($\delta$) is defined as the time from the time of initial decrease in diameter to the time of diameter return to baseline. Contraction interval (i) is the duration between the start of consecutive, repetitive contractions. Contraction magnitude ($\mu$) is the change in diameter from baseline to the nadir diameter. Contraction wave velocity is measured as the slope of the line both from the start of contraction ($v_1$) and from the minimal contraction diameters ($v_2$).

FIG. 7D shows a depiction of example contraction-associated intra-bag pressure changes. Pressure (bottom) and 16-channel diameter changes of the first three repetitive, antegrade contractions (RACs) in the same subject depicted in FIGS. 7A-C. The gray-shaded boxes indicate times during which the intra-bag pressure is increasing. The increase in pressure appears to occur during periods of decreasing diameter in the proximal impedance channels, but before the diameter begins to decrease in the distal channels (i.e. 2-5 cm above the EGJ). In the distal channels, an increase in diameter above the baseline diameter is temporally associated with the increasing intra-bag pressure and decreasing diameter in the proximal channels; the 22-mm diameter threshold is indicated by the red horizontal lines. The increasing pressure also coincides temporally with the nadir and subsequent increasing diameter of measurement channels located within the EGJ associated with the preceding RAC; however, pressure changes are observed with the first RAC (and thus independent of EGJ nadir diameter) in subjects displaying RACs.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

Some or all of the system, apparatus, and/or article of manufacture components described above, or parts thereof, can be implemented using instructions, code, and/or other software and/or firmware, etc. stored on a machine accessible or readable medium and executable by, for example, a processor system (e.g., the example processor system 610 of FIG. 6). When any of the appended claims are read to cover a purely software and/or firmware implementation, at least one of the components is hereby expressly defined to include a tangible medium such as a memory, DVD, CD, Blu-ray, etc. storing the software and/or firmware.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

One or more of the components of the systems and/or steps of the methods described above may be implemented alone or in combination in hardware, firmware, and/or as a set of instructions in software, for example. Certain embodiments may be provided as a set of instructions residing on a computer-readable medium, such as a memory, hard disk, Blu-ray, DVD, or CD, for execution on a general purpose computer or other processing device. Certain embodiments of the present invention may omit one or more of the method steps and/or perform the steps in a different order than the order listed. For example, some steps may not be performed in certain embodiments of the present invention. As a further example, certain steps may be performed in a different temporal order, including simultaneously, than listed above.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like.

Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of embodiments of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

It may be noted that operations performed by elements disclosed and described above (e.g., operations corresponding to process flows or methods discussed herein, or aspects thereof) may be sufficiently complex that the operations may not be performed manually by a human being within a reasonable time period.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method comprising:
inflating a measurement device positioned with respect to an esophageal body to trigger esophageal reactivity, the measurement device configured to measure a change in the impedance derived cross-sectional area and pressure of the esophageal body over a period of time to examine the shape of the esophagus;
capturing measurement data including the impedance derived cross-sectional area and the pressure of the esophageal body via the measurement device;
creating, by a computer processor, a time-based topography plot from the measurement data;
analyzing, by the computer processor, the topography plot to determine esophageal reactivity based on Repetitive Antegrade Contractions given by the impedance derived cross-sectional area and pressure;
assessing, by the computer processor, esophageal function based on the determined esophageal reactivity; and
based on the assessing, outputting an indication of esophageal function via a user interface.

2. The method of claim 1, wherein the measurement device includes an inflatable balloon positioned with respect to the esophageal body to trigger a physical reaction by conforming to available space in the esophageal body.

3. The method of claim 2, wherein a distension of the balloon and a physiological response to the distension are indicative of a health condition.

4. The method of claim 3, wherein the health condition includes at least one of stricture, eosinophilic esophagitis, or achalasia.

5. The method of claim 1, wherein the measurement device is configured to measure a plurality of impedance derived cross-sectional areas and a plurality of pressures of the esophageal body.

6. The method of claim 1, wherein the measurement device includes a functional lumen imaging probe including an inflatable portion and a pressure sensor.

7. A system comprising:
a measurement device positioned with respect to an esophageal body configured to inflate and trigger esophageal reactivity, the measurement device configured to measure a change in the impedance derived cross-sectional area and pressure of the esophageal body over a period of time to examine the shape of the esophagus; and a processor configured to:
create a time-based topography plot from the exported measurement data including the impedance derived cross-sectional area and the pressure of an esophageal body captured via the measurement device;
analyze the topography plot to determine esophageal reactivity based on Repetitive Antegrade Contractions given by the impedance derived cross-sectional area and pressure;
assess esophageal function based on the determined esophageal reactivity; and
based on the assessing, output an indication of esophageal function via a user interface.

8. The system of claim 7, wherein the measurement device includes an inflatable balloon positioned with respect to the esophageal body to trigger a physical reaction by conforming to available space in the esophageal body.

9. The system of claim 8, wherein a distension of the balloon and a physiological response to the distension are indicative of a health condition.

10. The system of claim 7, wherein the measurement device is configured to measure a plurality of impedance based cross-sectional areas and a plurality of pressures of the esophageal body.

11. The system of claim 7, wherein the measurement device includes a functional lumen imaging probe including an inflatable portion and a pressure sensor.

12. A tangible computer readable medium including instructions which, when executed by a processor, configure the processor to implement a method, the method comprising:
inflating a measurement device positioned with respect to an esophageal body to trigger esophageal reactivity, the measurement device configured to measure a change in the impedance derived cross-sectional area and pressure of the esophageal body over a period of time to examine the shape of the esophagus;
creating, by the processor a time-based topography plot from measurement data including the impedance derived cross-sectional area and the pressure of the esophageal body captured via the measurement device;
analyzing, by the processor, the topography plot to determine esophageal reactivity based on Repetitive Antegrade Contractions given by the impedance derived cross-sectional area and pressure;
assessing, by the processor, esophageal function based on the determined esophageal reactivity; and
based on the assessing, outputting an indication of esophageal function via a user interface.

13. The computer readable medium of claim 12, wherein the measurement device includes an inflatable balloon positioned with respect to the esophageal body to trigger a physical reaction by conforming to available space in the esophageal body.

* * * * *